(12) United States Patent
Langguth et al.

(10) Patent No.: US 8,399,523 B2
(45) Date of Patent: Mar. 19, 2013

(54) QUARTERNIZATION OF THE ADDITIVE AMINO ALKYLMETHACRYLATE COPOLYMER E FOR IMPROVING PERMEABILITY AND SOLUBILITY OF PHARMACEUTICALS

(75) Inventors: Peter Langguth, Biebergemuend (DE); Stefan Grube, Berlin (DE); Holger Frey, Emmendingen (DE); Boris Obermeier, Hattersheim (DE)

(73) Assignee: Evonik Roehm GmbH, Darmstadt (DE)

( * ) Notice: Subject to any disclaimer, the term of this patent is extended or adjusted under 35 U.S.C. 154(b) by 186 days.

(21) Appl. No.: 12/747,722

(22) PCT Filed: Dec. 12, 2008

(86) PCT No.: PCT/EP2008/010585
§ 371 (c)(1),
(2), (4) Date: Jun. 11, 2010

(87) PCT Pub. No.: WO2009/074336
PCT Pub. Date: Jun. 18, 2009

(65) Prior Publication Data
US 2010/0286288 A1    Nov. 11, 2010

(30) Foreign Application Priority Data

Dec. 13, 2007 (DE) .......................... 10 2007 060 175

(51) Int. Cl.
*A61K 47/32* (2006.01)
*C08F 26/02* (2006.01)
(52) U.S. Cl. ..................... 514/772.6; 526/312
(58) Field of Classification Search ........................ None
See application file for complete search history.

(56) References Cited

U.S. PATENT DOCUMENTS

| 6,231,885 | B1 | 5/2001 | Carrara |
| 6,632,454 | B2 * | 10/2003 | Beckert et al. ................ 424/482 |
| 2004/0197357 | A1 | 10/2004 | Heming et al. |
| 2006/0116290 | A1 | 6/2006 | Heming et al. |

FOREIGN PATENT DOCUMENTS

| EP | 0 913 158 | 5/1999 |
| EP | 1 810 668 | 7/2007 |
| WO | 02 100525 | 12/2002 |
| WO | 2004 052099 | 6/2004 |

OTHER PUBLICATIONS http://eudragit.evonik.com/product/eudragit/en/products-services/eudragit-products/protective-formulations/e-po/pages/default.aspx as referenced on Mar. 9. 2012.*
http://eudragit.evonik.com/product/eudragit/en/products-services/eudragit-products/protective-formulations/e-100/pages/default.aspx as referenced on Mar. 9, 2012.*
European Search Report issued Dec. 6, 2010, in Patent Application No. 08 860 544.9.
Xinke Cao et al. "Preparation and Characterization of a Novel Aqueous Dispersion of Eudragit E for Coating", Asian Journal of Pharmaceutical Sciences 2007, 2 (1),Mar. 13, 2007, pp. 29-37.
"Excipients Methacrylate-Based Coatings", http://www.pformulate.com/methacrylates.htm, Nov. 29, 2010, pp. 1-3.

* cited by examiner

*Primary Examiner* — Robert A Wax
*Assistant Examiner* — Jessica Worsham
(74) *Attorney, Agent, or Firm* — Oblon, Spivak, McClelland, Maier & Neustadt, L.L.P.

(57) ABSTRACT

The present invention relates to a strategy for improving the permeability and solubility of pharmaceuticals, based on adding a chemically modified amino alkyl methacrylate copolymer E, wherein the chemical modification is the quaternization of a fraction of the existing amino alkyl groups.

9 Claims, 12 Drawing Sheets

QUARTERNIZATION OF THE ADDITIVE AMINO ALKYLMETHACRYLATE COPOLYMER E FOR IMPROVING PERMEABILITY AND SOLUBILITY OF PHARMACEUTICALS

The present invention represents a strategy for improving the permeability and solubility of pharmaceuticals, which is based on addition of a chemically modified aminoalkyl methacrylate copolymer E, wherein the chemical modification consists of quaternization of a proportion of the aminoalkyl groups that are present.

The low bioavailability of many pharmaceuticals is a considerable problem in pharmaceutical formulation. Bioavailability, with respect to a particular route of application, is determined primarily by the solubility and the permeability of the active substance. Poor solubility with good permeability is just as likely to lead to poor bioavailability as is good solubility with poor permeability. Various strategies are pursued in order to overcome solubility and permeability problems.

The permeability of a substance in the intestine can for instance be increased by using particular excipients. Such excipients are for example chitosan or sodium caprate. It is assumed that these substances mainly have an influence on paracellular transport (Current Drug Delivery, 2005, 2, 9-22). However, it is also conceivable that there is a positive influence on transcellular transport.

For aminoalkyl methacrylate copolymer E (Pharmacopeia Japonica; listed as "Basic butylated methacrylate copolymer" in the European Pharmacopoeia) it was shown that in simultaneous oral administration with tetracycline, its AUC ("Area under the curve"=a measure of the total amount of a medicinal product that is absorbed by the body) is increased (EP 1302201 A1). Moreover, Eudragit E 100, a commercially available form of aminoalkyl methacrylate copolymer E (Röhm GmbH), can reduce the complexing of cationic active substances with mucus or bile acids (Takemura, Controlled Release Society 32nd Annual Meeting and Exposition; EP 1302201 A1; Macromol. Biosci., 2005, 5, 207-213). Moreover, Alasino et al. were also able to show that doxorubicin-loaded liposomes released more active substance in the presence of Eudragit E 100 without any change in liposome size, than in the absence of Eudragit E 100 (Macromol. Biosci., 2005, 5, 207-213). This indicates a permeability-altering action of Eudragit E 100 on lipid membranes. The mechanism by which Eudragit E 100 was able to increase the bioavailability has not yet been investigated explicitly. Possible mechanisms are the binding of bile acids, prevention of binding of the pharmaceutical to mucus and interaction of Eudragit E 100 with the cell membrane or the tight junctions.

FIG. 1 shows a representation of aminoalkyl methacrylate copolymer E (Eudragit E) that is commonly used in the literature. It can be seen from this that it is a random terpolymer and not a triblock copolymer, i.e. the values of m, n and o can vary.

European Patent EP 1302201 A1 describes the use of an aminoalkyl methacrylate copolymer E in combination with an acid. The compound is specified more precisely as Eudragit E in paragraph [0052]. Addition of an acid is necessary, as this compound has poor solubility at pH above 5.5, but it is ineffective in the undissolved state.

One problem to be solved by the present invention was to modify aminoalkyl methacrylate copolymer E chemically so that its solubility is increased significantly at pH above 5.5, without the addition of other substances, such as acids. Another problem to be solved by the present invention was that said chemical modification should not reduce the permeability-promoting action of aminoalkyl methacrylate copolymer E. Furthermore, said modified aminoalkyl methacrylate copolymer E must not be toxic and it should be possible to manufacture it efficiently in terms of time and cost.

The aforementioned problems are solved by the present invention with an aminoalkyl methacrylate copolymer E, which is characterized in that a proportion of the aminoalkyl groups is quaternized.

Preferably said proportion of quaternized aminoalkyl groups, relative to the total number of aminoalkyl groups, is more than 10%, preferably more than 20%. The degree of quaternization is, however, always less than 100%.

In a preferred embodiment said aminoalkyl methacrylate copolymer E has the structural formula:

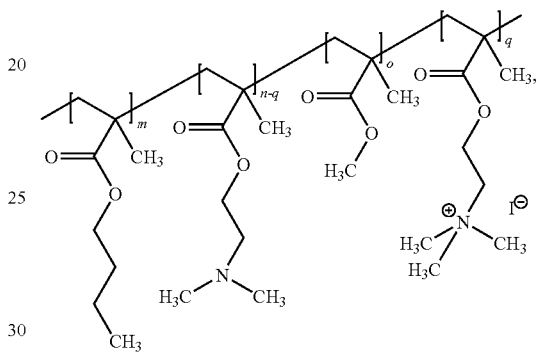

where m denotes the total number of butyl methacrylate groups,
n denotes the total number of aminoalkyl groups,
o denotes the total number of methyl methacrylate groups, and
q denotes the total number of quaternized aminoalkyl groups.

The problems are also solved by the present invention with a method of production of an aminoalkyl methacrylate copolymer E as characterized above, wherein said quaternization takes place by reaction with a methyl halide or dimethyl sulfate.

In a preferred embodiment said methyl halide is selected from the group comprising methyl iodide, methyl bromide, methyl chloride, preferably methyl iodide.

Methanol is preferably used as solvent in this method.

Moreover, the present invention relates to the use of an aminoalkyl methacrylate copolymer E as characterized above for improving the permeability and solubility of a pharmaceutical.

In a preferred embodiment said copolymer is administered together with said pharmaceutical.

The problems are also solved by the present invention with a pharmaceutical formulation that contains one or more pharmaceuticals and an aminoalkyl methacrylate copolymer E as characterized above.

The inventors found, surprisingly, that quaternized derivatives (degree of quaternization >20%) of aminoalkyl methacrylate copolymer E are able to produce a transient increase in the permeation of substances with low permeability without irreversible damage to the barrier function of the monolayer. The rates of increase are at least as high as, and sometimes much higher than, those achieved with nonquaternized aminoalkyl methacrylate copolymer E.

The sometimes much greater permeability-promoting action of the quaternized aminoalkyl methacrylate copolymer E was not to be expected at the outset, as charged molecules are known to have, because of their reduced lipid solubility, lower permeability coefficients through epithelia and endothelia, in comparison with their uncharged structural analogs. As an example we may mention the pair of substances scopolamine and N-butylscopolamine. This last-mentioned compound is a quaternary ammonium compound (with a permanent cationic charge), which displays only a slight absorption rate from the intestine and no notable passage across the blood-brain barrier. This can be attributed to the inadequate lipid solubility and interaction of the molecule with biological membranes.

Moreover, it could be shown that the transepithelial electrical resistance (TEER), as a measure for the permeability of the monolayer when cells are incubated with quaternized polymers, also decreases at pH 7.4, whereas this is not so for the original aminoalkyl methacrylate copolymer E. It can therefore be concluded that the solubility and action of the quaternized derivatives is pH-independent. Therefore, in contrast to the teaching of EP 1302201 A1, the present invention does not require the addition of an acid. This gives an advantage for oral administration, as the pH in the intestine is between 5.5 and 7.4 depending on the region. This property made it possible in vivo to improve the permeation of pharmaceuticals with low permeability and thus permitted their development and use as medicinal products.

Use of the substances according to the invention as bioavailability promoters is conceivable for almost any method of application. These can be solutions, suspensions, emulsions, inserts or other suitable pharmaceutical forms. Moreover, the invention can be used for the oral, cutaneous, buccal, rectal, nasal or any other method of application in which an absorption barrier has to be overcome, to permit local or systemic action of a pharmaceutical. For instance, use for opthalmological purposes is conceivable, i.e. application on the eye. In this case the substances could improve the penetration of certain pharmaceuticals through the cornea.

The method according to the invention for production of the quaternized derivatives is (even on a large scale) simple to carry out and moreover is efficient in terms of time and cost.

DEFINITIONS

The term "permeability", as used here, means the diffusion of a substance, for instance a medicinal product, through cell membranes, in particular epithelial cell membranes. The terms "cell permeability" or "epithelial permeability" can be used synonymously.

The term "degree of quaternization" denotes the proportion of quaternary nitrogen atoms (or quaternary aminoalkyl groups) relative to the total number of nitrogen atoms (aminoalkyl groups) in a given amount of aminoalkyl methacrylate copolymer E.

The term "pharmaceutical" denotes substances and preparations of substances that are intended for use on or in the body of a human or of an animal, in order to:
 heal, alleviate, prevent or recognize diseases, disorders, physical defects or ailments,
 protect against or remove pathogens, parasites or exogenous substances, or render them harmless,
 recognize or influence the condition, the state or the functions of the body or mental states, and
 replace active substances or body fluids produced by the body of a human or of an animal.

The term "bioavailability" denotes a pharmacological measure of the proportion of a substance that is available unchanged in the systemic circulation (especially: in the blood circulation). It shows how quickly and to what extent the substance (pharmaceutical) is absorbed and is available at the site of action.

"Eudragit E 100" (Röhm GmbH) is a commercially available form of aminoalkyl methacrylate copolymer E (alternative names: poly(butyl methacrylate, (2-dimethylaminoethyl) methacrylate, methyl methacrylate) and "Basic butylated methacrylate copolymer"). "Eudragit E PO" (also Röhm GmbH) is the powder form of Eudragit E 100.

FIGURES

EXAMPLES

1. Quaternization of Eudragit E PO

The monomer composition of Eudragit E PO (Röhm GmbH) was determined by $^1$H NMR spectroscopy (FIG.

2/Table 1). The deuterated solvent MeOH$_{d4}$ used for this was obtained from Deutero GmbH.

TABLE 1

Monomer composition of the polymer Eudragit E PO.

| | BMA (m) | DMAEMA (n) | MMA (o) |
|---|---|---|---|
| $^1$H NMR | 0.75 | 1.57 | 1 |
| Figures given by manufacturer | 1 | 2 | 1 |

BMA = butyl methacrylate, DMAEMA = (2-dimethylaminoethyl) methacrylate, MMA = methyl methacrylate.

Figure 1:
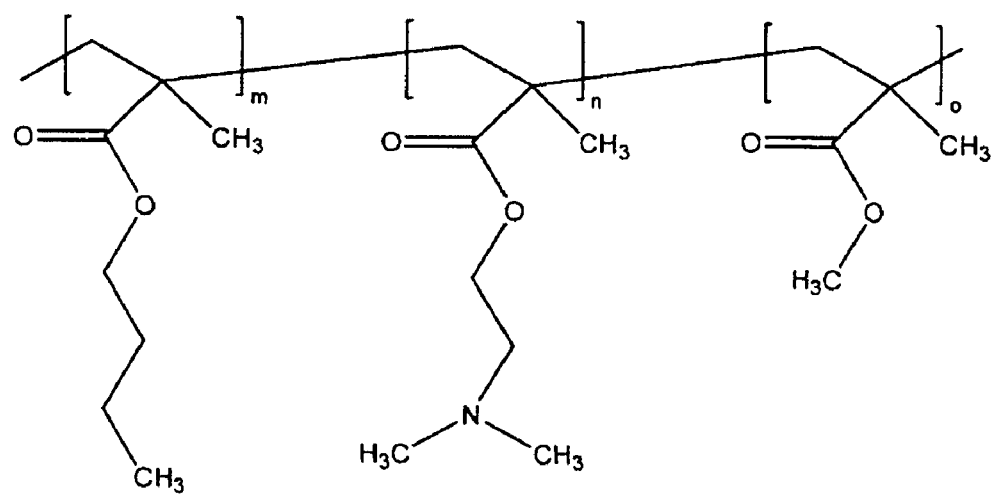
FIG. 1 shows the structural formula of aminoalkyl methacrylate copolymer E (Eudragit E).
Figure 2:
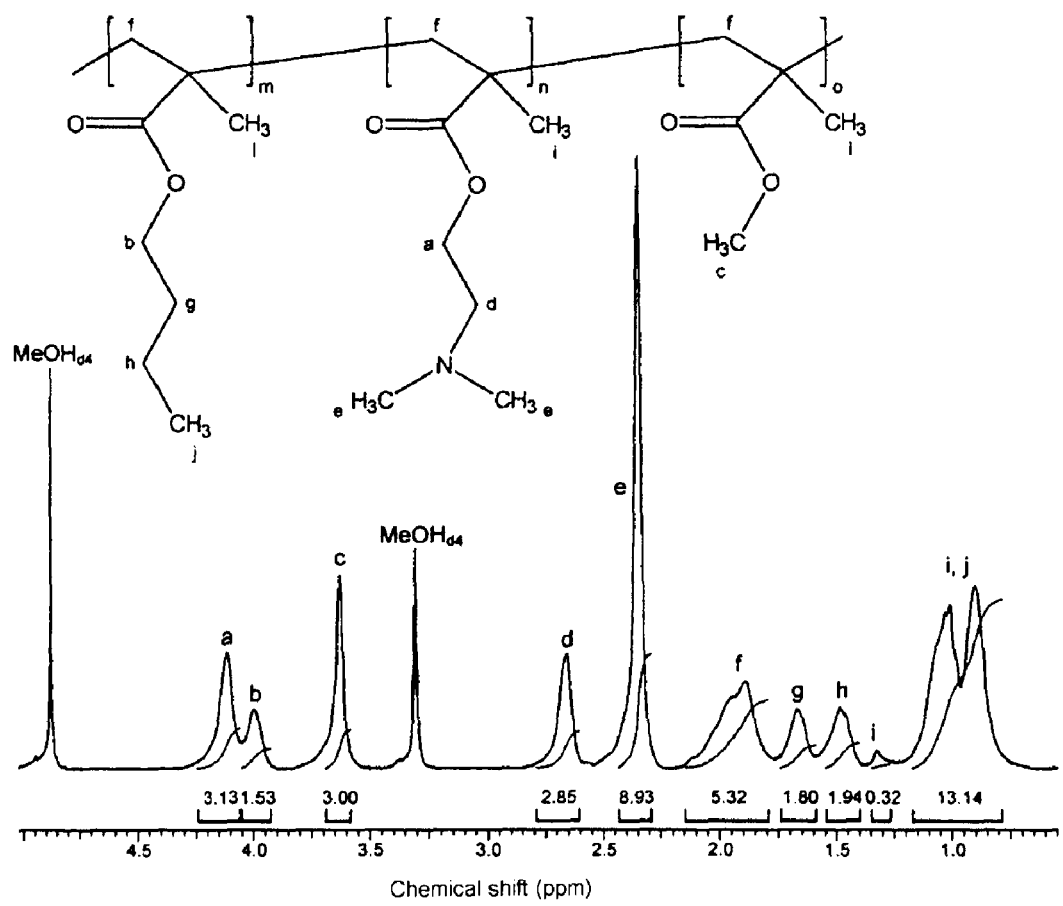
FIG. 2 shows the $^1$H NMR spectrum (300 MHz, MeOH$_{d4}$) of Eudragit E PO (Röhm GmbH) for determination of its monomer composition. The assignment of the signals is indicated by the letters a through j.
Figure 3:
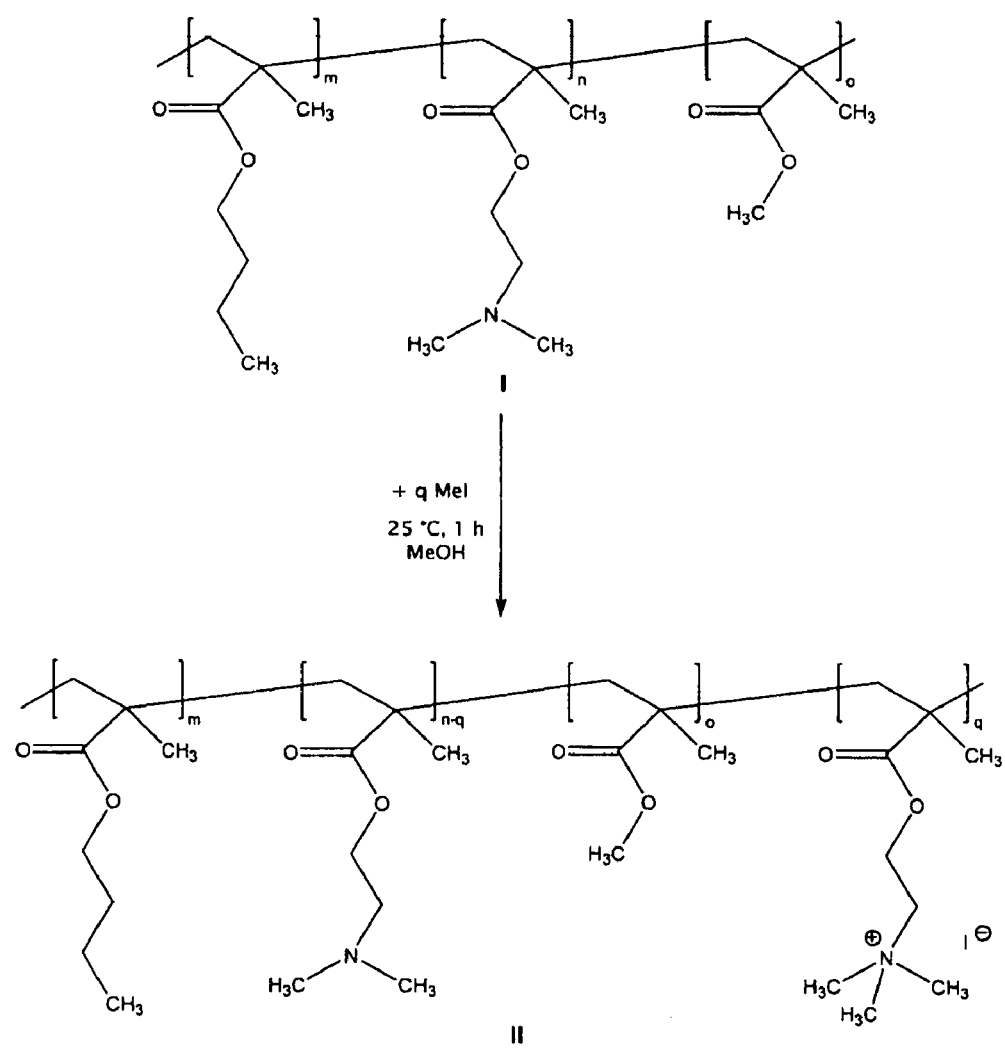
FIG. 3 shows the reaction scheme of the quaternization of Eudragit E PO (Röhm GmbH) with methyl iodide.

Defined quaternized Eudragit E PO was prepared by bimolecular nucleophilic substitution on methyl iodide (MeI) with the tertiary amine groups of Eudragit E PO. For a typical quaternization reaction (FIG. 3), Eudragit E PO was dissolved in a single-necked flask in methanol (MeOH) (0.1 g/ml; Acros Organics), in which both the starting compound and the corresponding quaternized product have good solubility. The amount of MeI (Acros Organics) required for the desired degree of quaternization was weighed and was added to the stirred solution. For methylation, approx. 10% less MeI was used than would be required theoretically for the desired degree of quaternization, according to the manufacturer's data for the monomer composition of Eudragit® EPO (Table 1). As the actual proportion of DMAEMA relative to BMA and MMA together is 10% lower, reduction of the amount of MeI is necessary. After 1-2 h, the polymer was precipitated by slow dropwise addition to 20 times the volume of vigorously stirred diethyl ether at −78° C.

Figure 4:
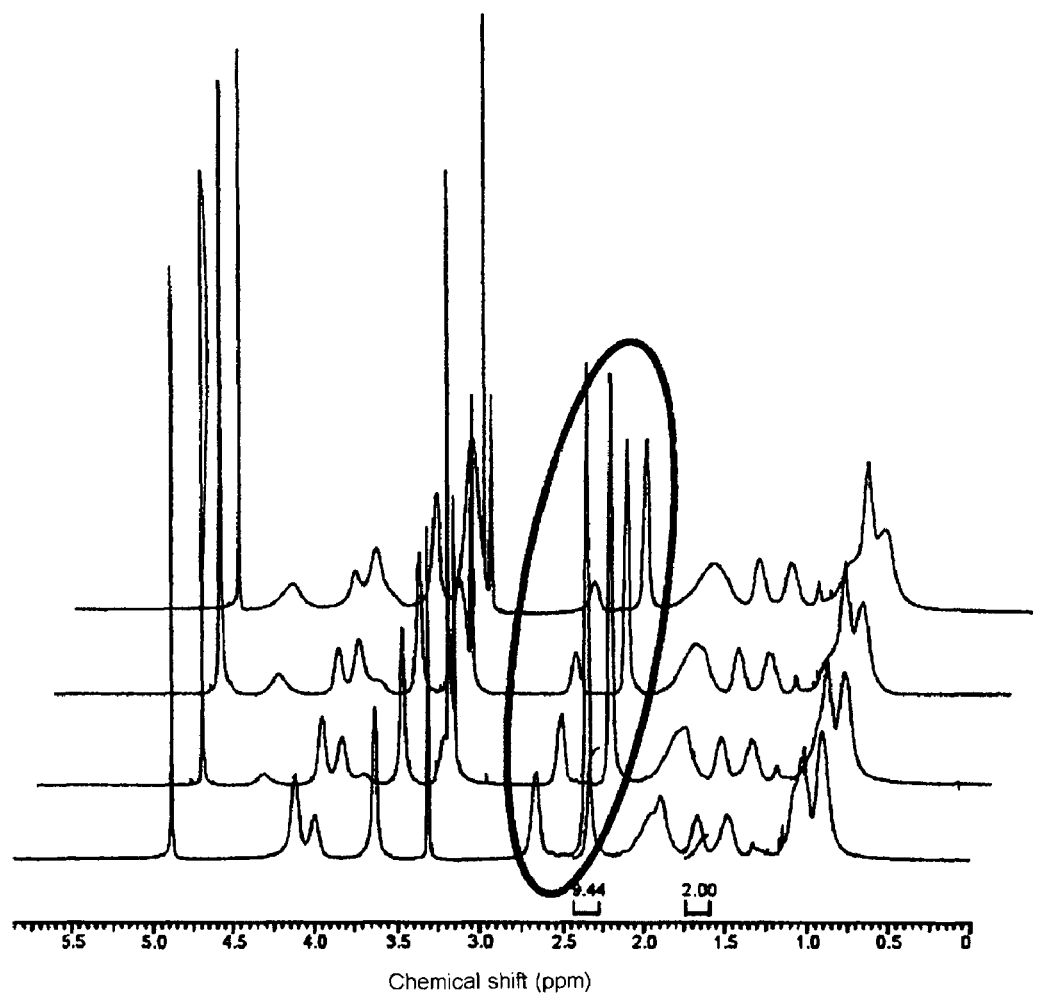
FIG. 4 shows the $^1$H NMR spectrum (300 MHz, MeOH$_{d4}$) of Eudragit E PO (Röhm GmbH) with a degree of quaternization of 0%, 22%, 42% and 65% (from bottom to top); the signals of the protons of the methyl and methylene groups bound to the tertiary nitrogen are shown against a gray background.

For $^1$H NMR determination of the degree of quaternization attained, a sample was taken and was dried in high vacuum. Quaternization of the nitrogen or introduction of a positive charge leads to a decrease in electron density on the bound groups. In the $^1$H NMR spectrum this deshielding is seen as a pronounced low-field shift. Therefore the degree of quaternization can be determined from the reduction in size of the signals of the groups bound to the tertiary nitrogen. Assuming constant monomer composition of the starting compound, in all spectra shown in FIG. 4 the integral of the signal of the methylene group of the butyl residue of BMA at 1.66 ppm as reference was set to 2. Then from the signal of the protons of the methyl groups bound to the tertiary nitrogen, integration was performed over exactly the same segment ($I_{Methyl}$) in all spectra. In the starting compound the value of this integral is 9.44. Therefore the proportion of quaternary nitrogen atoms relative to the total number of nitrogen atoms, i.e. the degree of quaternization $DQ_n$, is found from the formula:

$$DQ_n = 100\% - \frac{I_{Methyl} \cdot 100\%}{9,44}$$

$^1$H NMR signals for Eudragit E PO with a degree of quaternization of 65%:
$^1$H NMR (300 MHz, MeOH$_{d4}$) δ=4.52 (br, COOCH$_2$CH$_2$N(CH$_3$)$_3$$^+$), 4.12 (br, COOCH$_2$CH$_2$N(CH$_3$)$_2$), 3.91 (br, COOCH$_2$CH$_2$CH$_2$CH$_3$), 3.64 (br, COOCHA, 3.42 (br, COOCH$_2$CH$_2$N(CH$_3$)$_3$$^+$), 2.68 (br, COOCH$_2$CH$_2$N(CH$_3$)$_2$), 2.35 (br, COOCH$_2$CH$_2$N(CH$_3$)$_2$), 2.21-1.75 (br, CH$_2$ backbone), 1.65 (br, COOCH$_2$CH$_2$CH$_2$CH$_3$), 1.46 (br, COOCH$_2$CH$_2$CH$_2$CH$_3$), 1.30 (br, CH$_3$), 1.23-0.69 (br, CH$_3$, COOCH$_2$CH$_2$CH$_2$CH$_3$)

Figure 5:
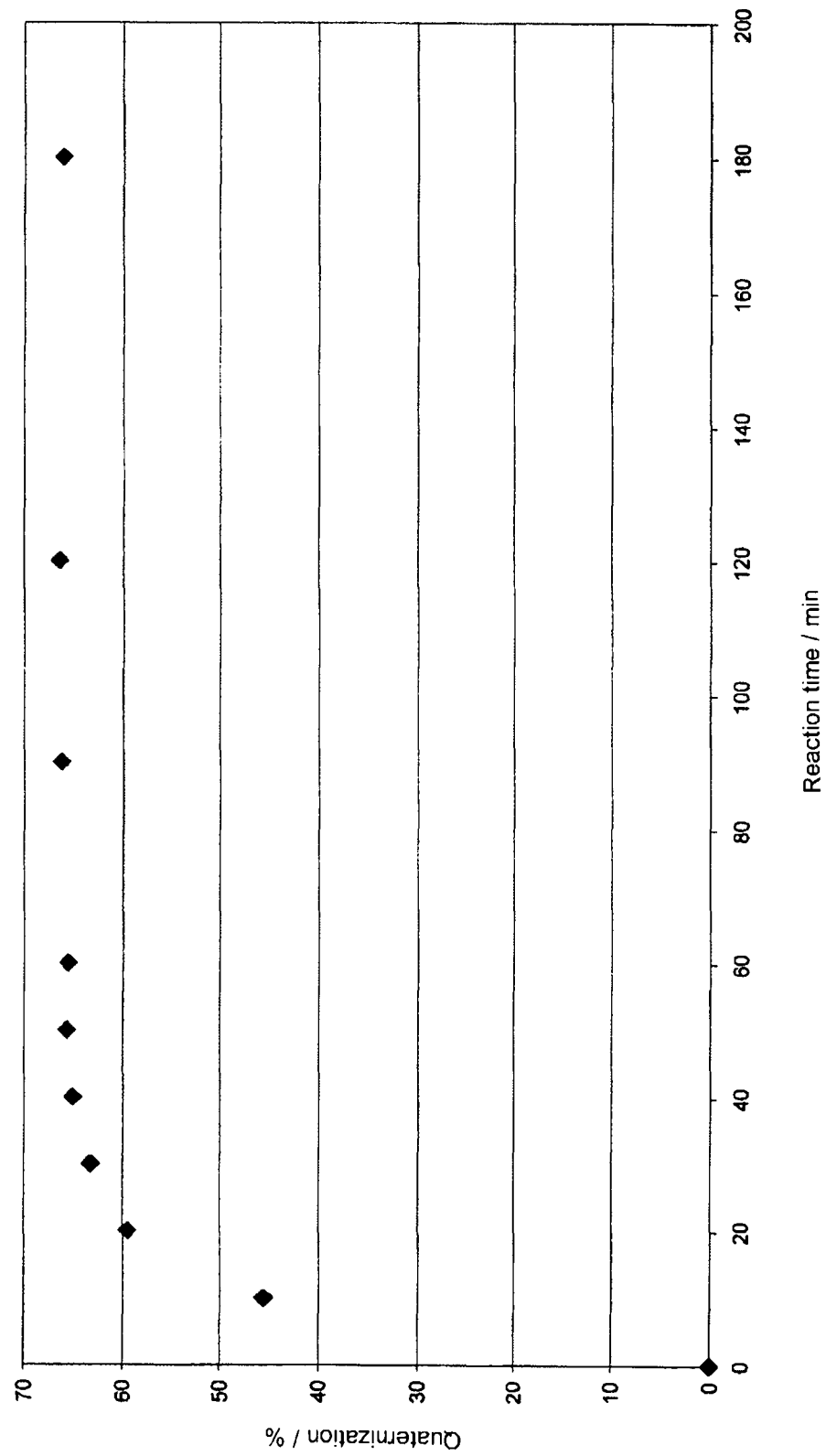
FIG. 5 shows the degree of quaternization determined by $^1$H NMR spectroscopy plotted against time at a final quaternization of 65%.

To monitor the course of the reaction, samples were taken from the reaction mixture for 65% quaternization. By removing all volatile constituents from the reaction mixture in high vacuum, the reaction was stopped in each case. FIG. 5 shows the typical saturation curve that is to be expected for the $S_N2$ reaction (=bimolecular, nucleophilic substitution), which takes place according to second-order kinetics. The desired degree of quaternization is reached after just one hour, and conversion is quantitative.

After quaternization of Eudragit E PO with methyl iodide, iodide is the counter-ion to the positively charged ammonium groups. In the cell experiments, so that effects that are not caused by the polymer itself can be excluded, ion exchange of iodide against the biochemically harmless chloride was carried out. The ion-exchange resin (Dowex Monosphere 550A, OH$^-$ loaded; Sigma Aldrich) was made into a slurry in water and was filled in an approx. 30 cm long column with approx. 3 cm diameter. The water at outlet had a pH of 8-9. Then it was rinsed with semi-concentrated acetic acid until the pH was in the acid range, and then with water until the water at outlet was neutral. Then 300 mg of the quaternized compound in 10 ml H$_2$O was added to the column and was rinsed with 300 ml water. 1 ml was taken and concentrated silver nitrate solution (Acros Organics) was added to it. If a precipitate was observed, the solution was added to the column again and then rinsed with 100 ml H$_2$O. The pH was adjusted to with HCl, acetic acid and water were removed by centrifugation, and the polymer was dried at 60° C. in the vacuum drying cabinet for several days. The end product was a colorless solid (yield: >95%).

2. Investigation of Quaternized Eudragit E PO Derivatives in the Caco-2 Cell Model A. Methods
Cell Culture Caco-2 cells were seeded at a density of 100 000 cells per cm$^2$ in 24-well polycarbonate Transwells (diameter: 0.33 cm$^2$). The cells were grown in DMEM, which was enriched with 100 units/ml penicillin, 100 mg/ml streptomycin, 1% nonessential amino acids and 10% FBS, at 5% CO$_2$ and 90% humidity. The experiments were conducted for 20 to 22 days after seeding.

To maintain the cell culture, cells were kept in reserve in 75 cm$^2$ cell culture bottles, which were trypsinized with a trypsin/EDTA solution (0.25%/0.02%) at 80-90% confluence and were supplied with fresh medium every other day. These cells were then trypsinized as described previously and seeded in Transwells for the experiments. The treatment with trypsin for detaching the cells is also called passaging. In this sense, only cells from passages 44-58 were used for the experiments.

Trypan Blue Exclusion Assay

First a solution of 0.04% trypan blue in 10 mM MES/HBSS (pH 6.5) was prepared. The Caco-2 cells were trypsinized, centrifuged and resuspended in 10 mM MES/HBSS (pH 6.5). Then the cells were incubated for 1 h in 1.5 ml Eppendorf vessels in 10 mM MES/HBSS (pH 6.5) with 0.21 µM polymer at room temperature on a turntable. 50 µl of the cell suspension was then mixed with 50 µl of the trypan blue solution, 20 µl of this mixture was transferred to a hemacytometer, and the cells were counted under a light microscope. In this test, intact cells are characterized by the fact that they exclude the dye trypan blue, whereas damaged/dead cells are stained blue.

Transport Recovery Assay for Mannitol

The assay was carried out in 24-well polycarbonate Transwells. The cells were incubated for 1 h with a solution of the polymer (0.21 µM), 0.1 mM mannitol and 1 µCi/ml $^{14}$C-mannitol in 25 mM MES/HBSS (pH 6.5) on the apical side and 25 mM HEPES/HBSS (pH 7.4) on the basolateral side. The apical and basolateral solutions were carefully removed after one hour and replaced with 25 mM MES/DMEM+10% FBS (pH 6.5) with 0.1 mM mannitol and 1 µCi/ml $^{14}$C-mannitol on the apical side and 25 mM HEPES/DMEM+10% FBS (pH 7.4) on the basolateral side. The polycarbonate inserts were transferred hourly to a new 24-well plate filled with buffer. Samples of the basolateral medium were used for scintillation counting. To determine the initial mannitol concentration, samples of the apical medium were taken at the beginning of the experiment and after exchange of the apical medium and were used for scintillation counting.

Transport Assay for Trospium

Trospium transport was analyzed by HPLC. The apical cell side was incubated with a transport buffer consisting of 10 mM MES/HBSS (pH 6.5), which contained the polymer at a concentration of 0.21 µM and 2 mM trospium, and the basolateral cell side was incubated in 10 mM HEPES/HBSS (pH 7.4). From the apical side, 100 µl samples were taken at the beginning of the experiment and were replaced with 100 µl of fresh buffer. After 120 min the transport experiment was stopped by removing the filtration units and samples were taken from the basolateral side. Until the samples were measured by HPLC they were stored at −18° C.

Transport Assay for Talinolol

Talinolol was used at a concentration of 1 µCi/ml. The apical side was incubated with polymer solution (0.21 µM) in 10 mM MES/HBSS buffer (pH 6.5) and the basolateral side in 10 mM HEPES/HBSS buffer (pH 7.4). At the beginning 20 µl samples were taken from the apical side and the donor chamber was refilled with 20 µl fresh solution. After 30, 60, 90 and 120 min, 500 µl samples were taken from the basolateral chamber and replaced in each case with 500 µl fresh buffer.

Scintillation Counting

The samples were analyzed in Mini Vials A-tubes (Carl Roth GmbH & Co, Karlsruhe, Germany) by means of a liquid-scintillation counter (LC 6000, Beckman Coulter, Unterschleißheim, Germany) after thorough mixing with 4 ml scintillation solution Rotiszint 22 (Carl Roth GmbH & Co, Karlsruhe, Germany). The counting time was set at 5 min for all samples and experiments.

HPLC

The measurements were carried out using a Jasco HPLC system, consisting of a Jasco PU-980 pump, a Jasco AS-950 sampler (Autosampler) and a Jasco UV-975 UV/VIS detector (Jasco Deutschland GmbH, Groß-Umstadt, Germany), using amezinium metilsulfate as internal standard.

Chromatography Conditions:
Column: LiChroCart 125×4 mm, RP-8, Superspher 60 (Merck Darmstadt, Germany)
Mobile phase: 0.01 M HEPES, 0.003 M $K_2HPO_4 \times 3H_2O$, 300 ml doubly-distilled water, 700 ml acetonitrile, 1.5 ml 85% phosphoric acid
Temperature: room temperature
Flow rate: 1.2 ml/min
Detection: UV absorption 210 nm
Injection volume: 50 µl
Run time: 7 min Measurement of Transepithelial Electrical Resistance (TEER)

TEER was measured using a so-called "Chopstick" electrode (Millicell ERS, Millipore, Bedford, USA). For the transport recovery tests, 24-well polycarbonate Transwells were used, and the cells were first incubated for 20 minutes apically with 25 mM MES/DMEM (pH 6.5) and basolaterally with 25 mM HEPES/DMEM+10% FBS (pH 7.4). Then concentrated polymer solutions were added by pipet, so that the final concentration of the polymer in the incubation media was 0.21 µM. The TEER was then monitored for an hour, after which the medium on the apical side was replaced with fresh buffer (25 mM MES/DMEM (pH 6.5)+10% FBS or 25 mM HEPES/DMEM (pH 7.4)+10% FBS). The recovery of the TEER was then monitored for 6 hours.

Calculation of $P_{app}$ (Apparent Permeation)

The $P_{app}$ values were calculated from the following formula: $P_{app}=(V_a/(A*t))*([pharmaceutical]_{acceptor}/[pharmaceutical]_{start,donor})$, where $V_a$ is the apical volume in the acceptor chamber in ml, A is the area of the monolayer in $cm^2$, t is the time in s, $[pharmaceutical]_{acceptor}$ is the cumulative concentration of pharmaceutical in the basolateral chamber after t seconds and $[pharmaceutical]_{start,donor}$ is the initial concentration of pharmaceutical in the donor chamber.

B. Results

Of the compounds synthesized according to point 1, three derivatives with a degree of quaternization of 22%, 42% and 65% were investigated in the Caco-2 model (J Pharm Sci., 2000, 89, 63-75).

Figure 6:
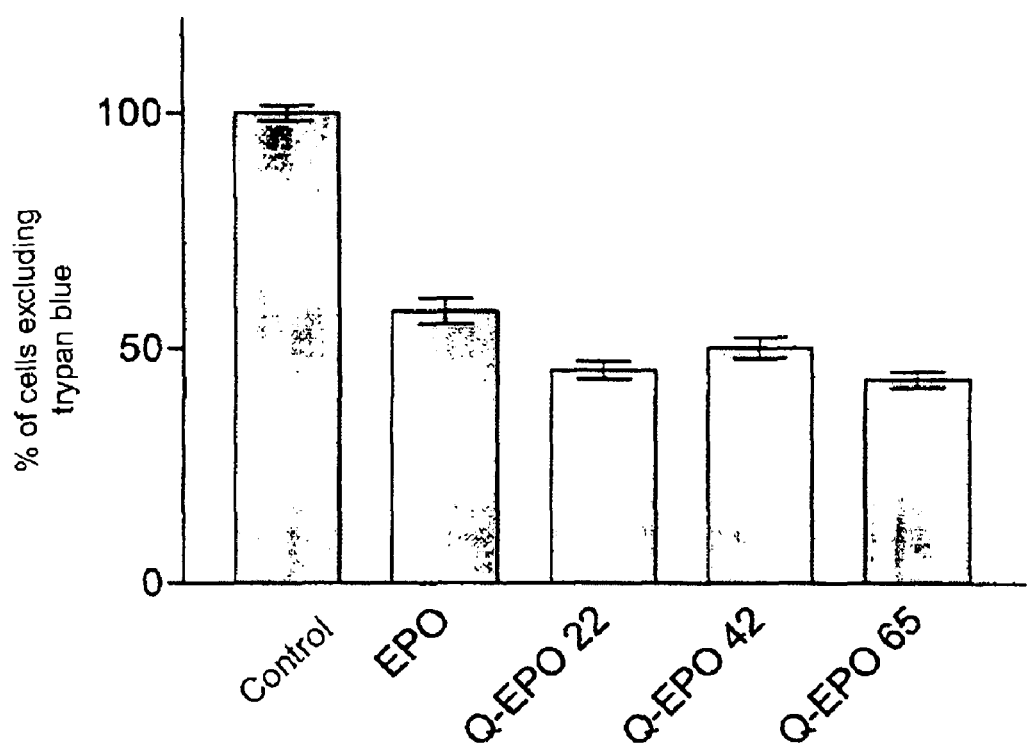
FIG. 6 shows a graph with the percentages of Caco-2 cells excluding trypan blue relative to the control, showing the standard deviation determined from 3 measured values at pH 6.5 after an incubation time of 1 h.
Figure 8:
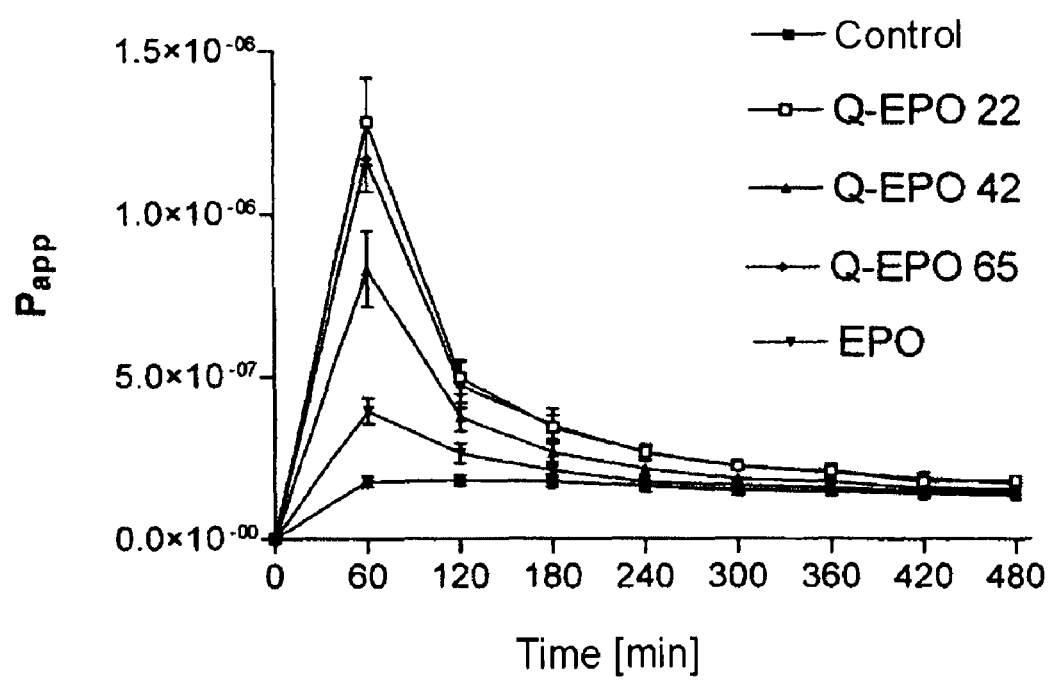
FIG. 8 shows a graph documenting the reversibility of mannitol permeability after 1 h incubation with equimolar amounts of polymer. $P_{app}$ was measured at intervals of 60 min.
Figure 9:
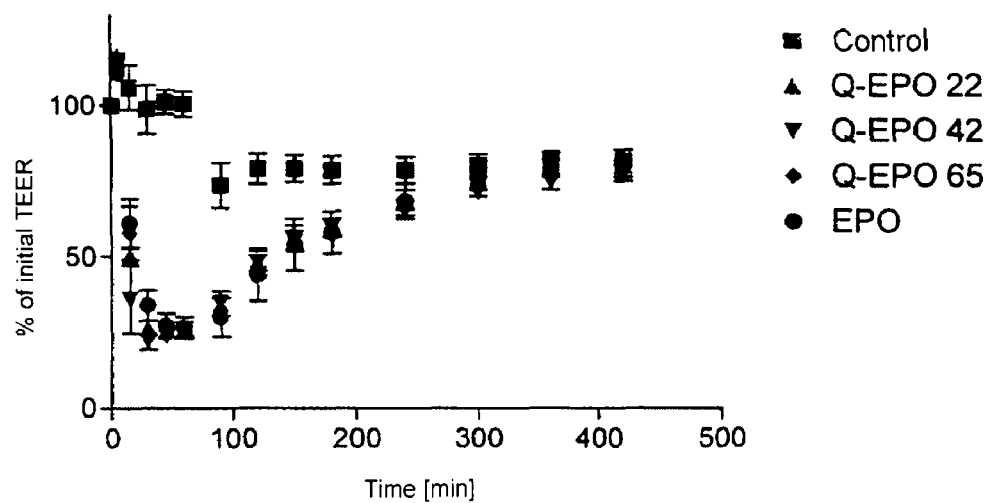
FIG. 9 shows the variation of the TEER values as a percentage of the TEER value at pH 6.5 apically and pH 7.4 basolaterally at the moment of addition of Eudragit E PO and quaternized derivatives thereof at a concentration of 0.21 µM after 1 h incubation in the presence of the polymer and 6 h incubation at pH 6.5 apically and pH 7.4 basolaterally without polymer compounds.

For investigating the toxicity of the quaternized derivatives of Eudragit E PO, first a trypan blue exclusion test was carried out. As can be seen from FIG. 6, the quaternized compounds have only a slightly higher toxicity than Eudragit E PO. In addition, both the transepithelial resistance (TEER) and the increase in mannitol transport during incubation of the cells with the quaternized compounds were reversible (FIGS. 8 and 9). This shows that the epithelium is not damaged irreversibly by the substances and after removal of the polymer solutions the barrier function is restored.

Figure 10:
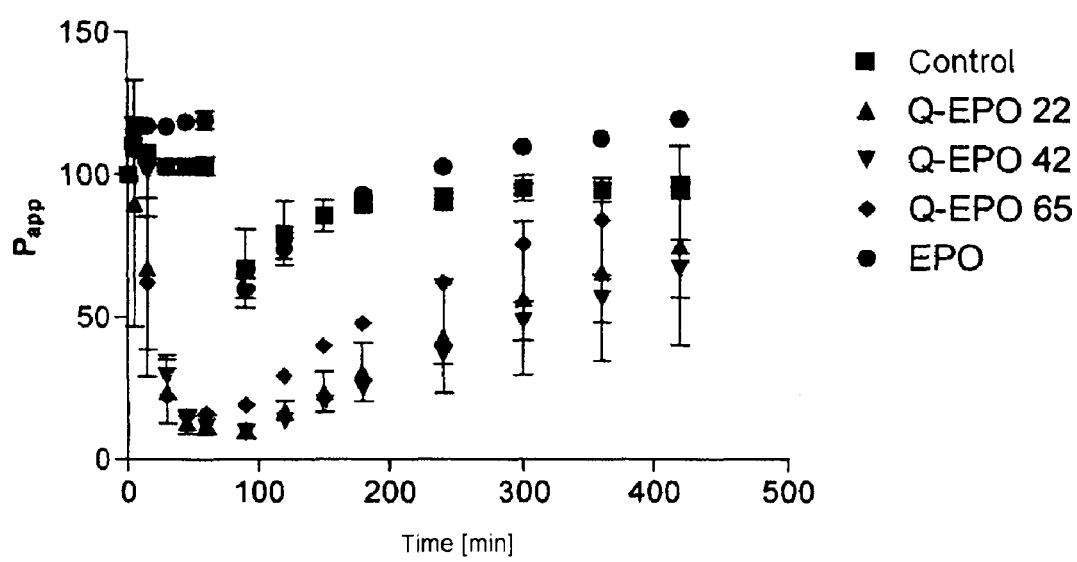
FIG. 10 shows the variation of the TEER values as a percentage of the TEER value at pH 7.4 apically and basolaterally at the moment of addition of Eudragit E PO and quaternized derivatives thereof at a concentration of 0.21 µM after 1 h incubation in the presence of the polymer and 6 h incubation without polymer compounds.

At pH of 7.4 (apically and basolaterally) Eudragit E PO in equimolar concentration to the quaternized derivatives displayed behavior with respect to the TEER comparable to the control, whereas the quaternized compounds caused a definite decrease in the TEER (FIG. 10). Possibly Eudragit E PO is not effective at neutral pH, owing to its poorer solubility.

Figure 7:
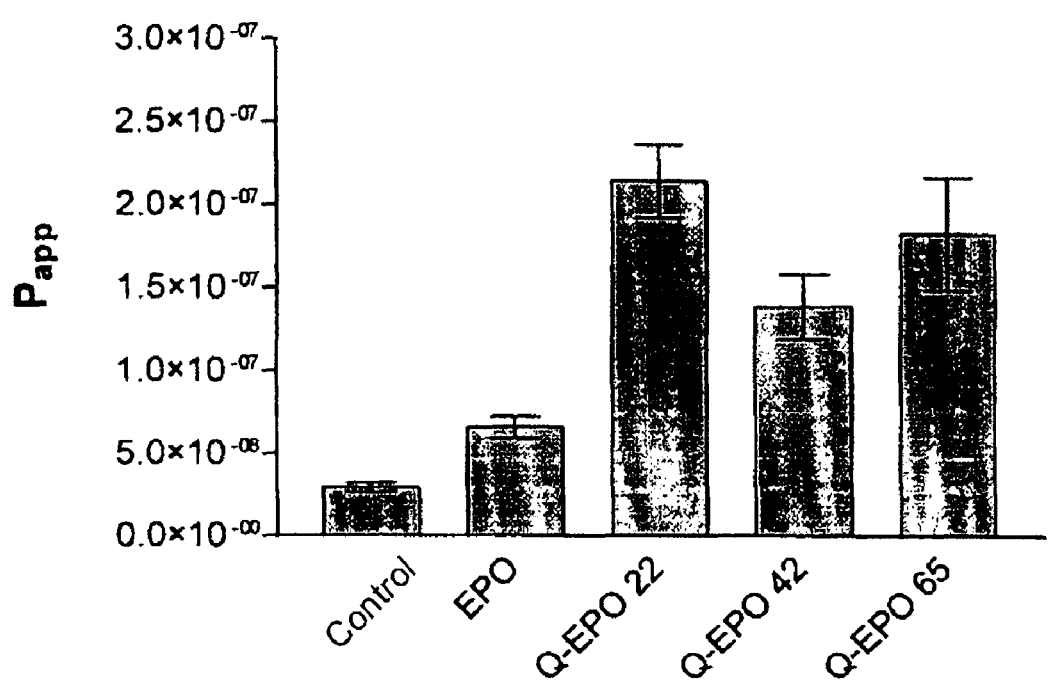
FIG. 7 shows a plot of $P_{app}$ (apparent permeability) with the standard deviation from 4 measured values for mannitol after 1 h incubation at pH 6.5 in the presence of Eudragit E PO and quaternized derivatives thereof.
Figure 11:
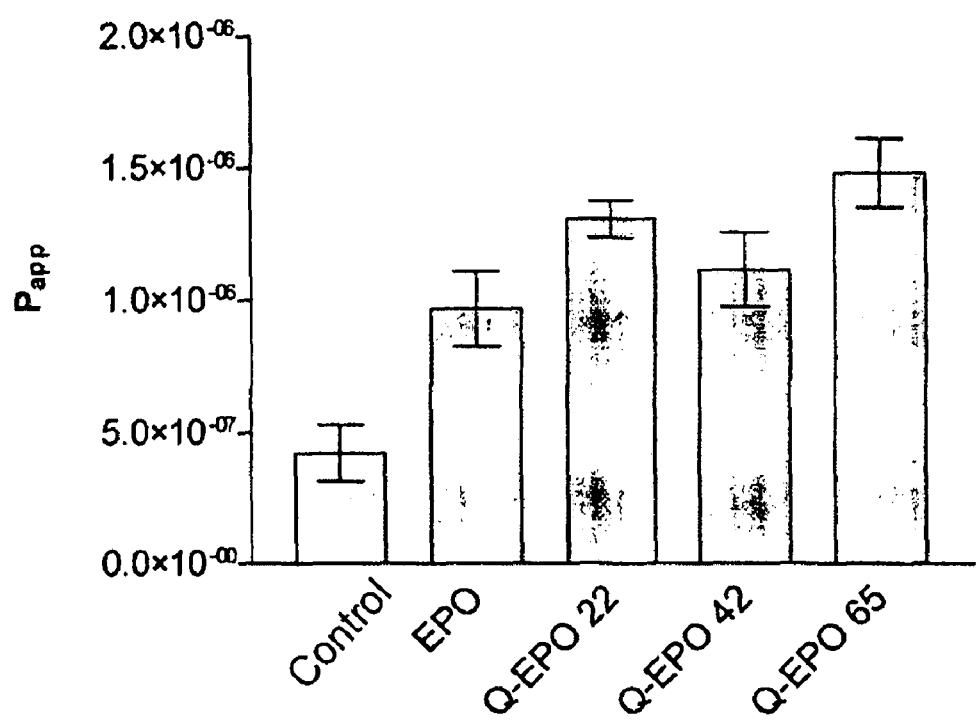
FIG. 11 shows a plot of $P_{app}$ with the standard deviation from 3-5 measured values for trospium chloride after 2 h incubation at pH 6.5 apically and pH 7.4 basolaterally and in the presence of Eudragit E PO and quaternized derivatives thereof at a concentration of 0.21 µM.
Figure 12:
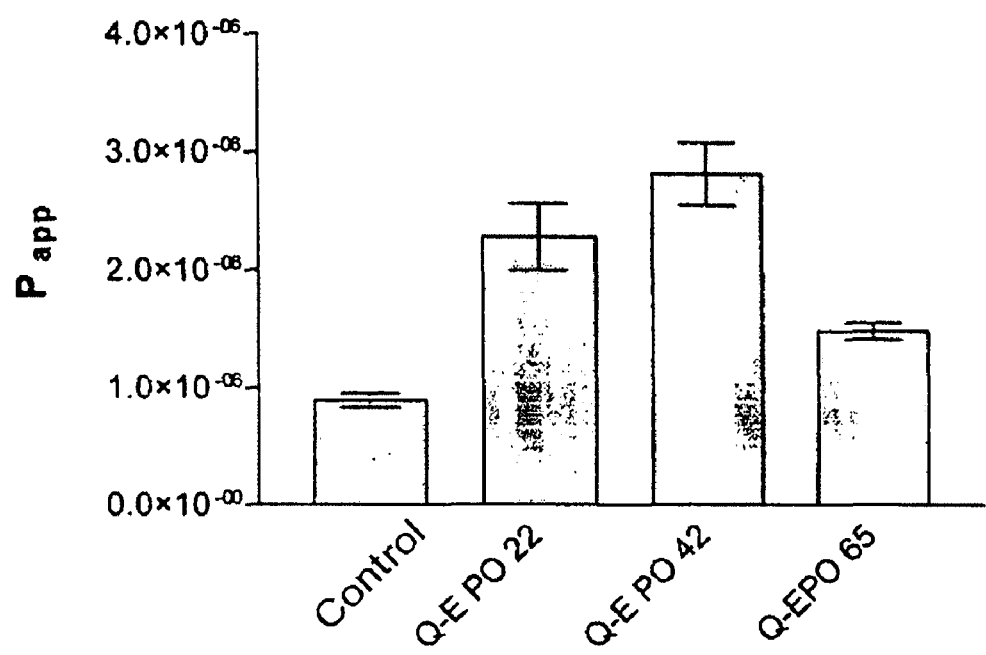
FIG. 12 shows a plot of $P_{app}$ with the standard deviation from 3 measured values for talinolol at pH 6.5 apically and pH 7.4 basolaterally and in the presence of the quaternized derivatives of Eudragit E PO at a concentration of 50 µg/ml.

Besides the increase in mannitol permeability (FIG. 7), in the cell culture model the polymer also increased the permeability of trospium (FIG. 11) and talinolol (FIG. 12). In the case of the mannitol and trospium permeability, equimolar amounts of the quaternized derivatives were compared with Eudragit E PO. It was found that in equimolar amount, the derivatives sometimes increase the permeability of the stated substances to a greater extent, but in any case at least to the same extent as Eudragit E PO.

The invention claimed is:

1. An aminoalkyl methacrylate copolymer E, comprising at least one quaternized aminoalkyl group and at least one non-quaternized aminoalkyl group, wherein the aminoalkyl methacrylate copolymer E has formula (I)

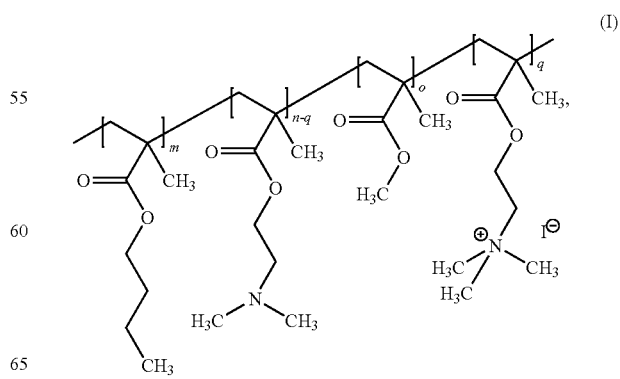

wherein m is the total number of butyl methacrylate groups, n is the total number of aminoalkyl groups, o is the total number of methyl methacrylate groups, q is the total number of quaternized aminoalkyl groups, and m, n, o and q are each at least 1; and wherein the proportion of the quaternized aminoalkyl groups relative to the total number of the aminoalkyl groups is more than 10% and less than 100%.

2. A method of producing the aminoalkyl methacrylate copolymer E according to claim 1, comprising reacting a methyl iodide with at least one aminoalkyl group of an aminoalkyl methacrylate copolymer precursor.

3. The method according to claim 2, wherein the reacting is carried out in the presence of methanol as a solvent.

4. A method for improving the permeability and solubility of a pharmaceutical composition, comprising administering an aminoalkyl methacrylate copolymer E according to claim 1 with the pharmaceutical composition.

5. A pharmaceutical formulation comprising at least one pharmaceutical compound and the aminoalkyl methacrylate copolymer E according to claim 1.

6. The aminoalkyl methacrylate copolymer E according to claim 1, wherein the proportion of the quaternized aminoalkyl groups relative to the total number of the aminoalkyl groups is more than 20% and less than 100%.

7. A pharmaceutical formulation comprising at least one pharmaceutical compound and an aminoalkyl methacrylate copolymer E according to claim 6.

8. The aminoalkyl methacrylate copolymer E according to claim 1, wherein the proportion of the quaternized aminoalkyl groups relative to the total number of the aminoalkyl groups is from 22 to 65%.

9. The aminoalkyl methacrylate copolymer E according to claim 1, wherein the aminoalkyl methacrylate copolymer with the quaternized aminoalkyl groups has a greater permeability-promoting action in comparison to an aminoalkyl methacrylate copolymer precursor.

* * * * *